United States Patent
Aduri et al.

(10) Patent No.: US 9,561,499 B2
(45) Date of Patent: Feb. 7, 2017

(54) PROCESS FOR REGENERATING IONIC COMPOUND

(71) Applicant: RELIANCE INDUSTRIES LIMITED, Mumbai, Maharashtra (IN)

(72) Inventors: Pavankumar Aduri, Maharashtra (IN); Parasu Veera Uppara, Maharashtra (IN); Viswanath Kotra, Andhra Pradesh (IN); Mangesh Sakhalkar, Maharashtra (IN); Vibhuti Dukhande, Maharashtra (IN); Vivek Prabhakar Raje, Maharashtra (IN)

(73) Assignee: RELIANCE INDUSTRIES LIMITED, Mumbai, Maharashtra (IN)

(*) Notice: Subject to any disclaimer, the term of this patent is extended or adjusted under 35 U.S.C. 154(b) by 0 days.

(21) Appl. No.: 14/783,536

(22) PCT Filed: Apr. 21, 2014

(86) PCT No.: PCT/IN2014/000253
§ 371 (c)(1),
(2) Date: Oct. 9, 2015

(87) PCT Pub. No.: WO2014/184803
PCT Pub. Date: Nov. 20, 2014

(65) Prior Publication Data
US 2016/0082426 A1     Mar. 24, 2016

(30) Foreign Application Priority Data
Apr. 19, 2013  (IN) .................... 1457/MUM/2013

(51) Int. Cl.
| C07D 213/06 | (2006.01) |
| C07D 233/58 | (2006.01) |
| B01J 31/02 | (2006.01) |
| B01J 31/26 | (2006.01) |
| B01J 31/40 | (2006.01) |
| C07C 2/66 | (2006.01) |

(52) U.S. Cl.
CPC ......... *B01J 31/0284* (2013.01); *B01J 31/0282* (2013.01); *B01J 31/26* (2013.01); *B01J 31/40* (2013.01); *C07C 2/66* (2013.01); *C07D 213/06* (2013.01); *C07D 233/58* (2013.01); *B01J 2231/323* (2013.01); *C07C 2527/125* (2013.01); *Y02P 20/52* (2015.11); *Y02P 20/584* (2015.11)

(58) Field of Classification Search
None
See application file for complete search history.

(56) References Cited

U.S. PATENT DOCUMENTS

| 7,651,970 B2 | 1/2010 | Elomari et al. |
| 7,674,740 B2 | 3/2010 | Harris et al. |
| 7,678,727 B2 | 3/2010 | Harris et al. |
| 7,691,771 B2 | 4/2010 | Harris et al. |
| 7,732,364 B2 | 6/2010 | Chang et al. |
| 7,737,067 B2 | 6/2010 | Elomari et al. |
| 7,884,045 B2 | 2/2011 | Harris et al. |
| 7,956,002 B2 | 6/2011 | Elomari et al. |
| 8,088,338 B2 | 1/2012 | Luo et al. |
| 8,597,517 B2 | 12/2013 | Guzmán Lucero et al. |
| 2010/0278699 A1 | 11/2010 | Luo et al. |
| 2011/0215052 A1 | 9/2011 | Guzmán Lucero et al. |
| 2011/0297618 A1 | 12/2011 | Luo et al. |

FOREIGN PATENT DOCUMENTS

| WO | 01/15175 A2 | 3/2001 |
| WO | 2009/085450 A1 | 7/2009 |

OTHER PUBLICATIONS

International Search Report of PCT/IN2014/000253, mailed Oct. 27, 2014.
Abu-Eishah, Ionic Liquids Recycling for Reuse, Ionic Liquids—Classes and Properties, Oct. 2011, pp. 239-273.

*Primary Examiner* — Zinna Northington Davis
(74) *Attorney, Agent, or Firm* — Collard & Roe, P.C.

(57) ABSTRACT

The present disclosure provides a process for regenerating the deactivated ionic compound. The process involves mixing a deactivated ionic compound with at least one solvent such as ethyl acetate and neutralizing with at least one base such as triethylamine and tert-butyl amine to obtain a precipitate. The obtained precipitate is filtered to obtain a residue which is then washed with a solvent such as dichloromethane to obtain the ionic compound.

9 Claims, 1 Drawing Sheet

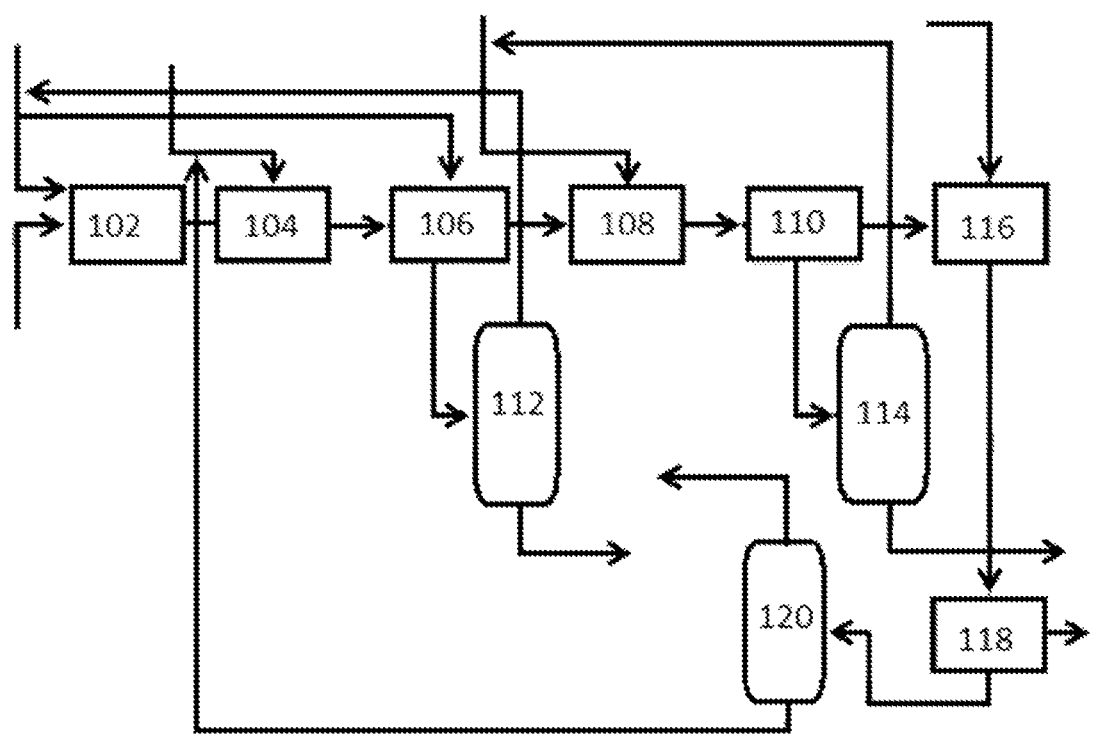

PROCESS FOR REGENERATING IONIC COMPOUND

CROSS REFERENCE TO RELATED APPLICATIONS

This application is the National Stage of PCT/IN2014/000253 filed on Apr. 21, 2014, which claims priority under 35 U.S.C. §119 of Indian Application No. 1457/MUM/2013 filed on Apr. 19, 2013, the disclosures of which are incorporated by reference.

FIELD OF THE DISCLOSURE

The present disclosure relates to a process for regenerating ionic compound. The present disclosure particularly relates to a process for regenerating halo metal based ionic compound.

BACKGROUND

Ionic compounds are compounds that are composed of ions i.e., cations and anions. Ionic compounds are suitable for use as a catalyst and as a solvent in alkylation reactions, polymerization, dimerization, oligomerization, acetylation, metatheses and copolymerization reactions.

The most common ionic compounds are those prepared from organic based cations and inorganic or organic anions. Pyridinium and imidazolium are frequently used cations whereas anions such as $BF_4^-$, $PF_6^-$, haloaluminates such as $Al_2Cl_7^-$ and $Al_2Br_7^-$, $[(CF_3SO_2)_2N)]^-$, alkyl sulphates ($RSO_3^-$), and carboxylates ($RCO_2^-$) are commonly employed. The catalytically interesting ionic compounds are those derived from ammonium halides and Lewis acids such as $AlCl_3$, $TiCl_4$, $SnCl_4$, $FeCl_3$.

Haloaluminate ionic compounds are ionic compounds derived from ammonium halides and $AlCl_3$ which are used for alkylation reactions. For instance, 1-butyl-3-methyl imidazolium bromide can be reacted with $AlCl_3$ to form fused [BMIM]$Al_2Cl_6$Br ionic compound which is used as a catalyst for alkylation reactions. Conjunct polymers are formed as by-products during the alkylation reactions employing ionic compound catalysts. These by-products deactivate the ionic compound catalyst by forming complexes with the ionic compound catalyst. The activity of the ionic compound catalyst decreases with repeated use of ionic compound catalyst which after a certain number of recycles needs to be replaced. Deactivation of ionic compound catalyst by by-products is problematic and adversely affects the economics of alkylation reactions. Therefore, commercial exploitation of ionic compound catalysts for alkylation reaction would be economical only if they can be efficiently regenerated and recycled.

Few methods were reported for removing the conjunct polymers and regenerating the ionic compound catalysts.

U.S. Pat. Nos. 7,651,970, 7,678,727, 7,691,771 and 7,884,045 disclose a process for regenerating a used chloroaluminate ionic liquid catalyst. The process consists of contacting the used chloroaluminate ionic liquid catalyst and hydrogen with a metal or homogeneous or supported hydrogenation catalyst in a reaction zone under hydrogenation conditions for a time sufficient to reactivate the ionic liquid catalyst.

U.S. Pat. No. 7,674,740 discloses the regeneration of used ionic liquid by contacting it with an iso-paraffin containing stream and Bronsted acid in a reaction zone.

U.S. Pat. No. 7,732,364 and WO 2009/085450 disclose the regeneration of used ionic liquid by contacting it with Aluminium metal in the presence of hydrogen to liberate conjunct polymers. United States Patent No. 20100278699 discloses the above method in a reactive extraction column.

WO 2001/15175 discloses the regeneration of imidazolium based ionic liquid such as 1-methyl-3-ethylimidazolim by subjecting it to thermolysis at 250° C. for 3 hrs at 2 mm Hg.

U.S. Pat. No. 7,737,067 discloses regeneration of deactivated 1-Butyl-pyridinium heptachloroaluminate by adding 1-Butyl-pyridinium chloride along with inert hydrocarbon ranging from $C_5$ to $C_8$. 1-Butyl-pyridinium chloride interacts with $AlCl_3$ species thereby liberating the conjunct polymer. The conjunct polymer thus released simultaneously gets solubilized in inert hydrocarbon layer. The 1-Butyl-pyridinium heptachloroaluminate obtained is further treated with $AlCl_3$ to fully restore the activity of the catalyst.

U.S. Pat. No. 7,956,002 discloses the method for regenerating an used acidic ionic liquid catalyst. The method consists of contacting the used ionic liquid catalyst with at least one metal in a regeneration zone in the presence of hydrogen under regeneration conditions for a time sufficient to activate the ionic liquid. The regeneration of the used ionic liquid can also be conducted in the presence of a hydrocarbon solvent.

U.S. Pat. No. 8,088,338 discloses an apparatus for regenerating an ionic liquid catalyst which has been deactivated by conjunct polymers. The apparatus consists of moving bed wherein slurry of ionic liquid and aluminium metal can be feed. Solvent and hydrogen gas (optional) are feed through the bottom of the reactor which remove conjunct polymer and regenerates the ionic liquid.

U.S. Pat. No. 8,597,517 discloses a process for regeneration of ionic liquids after being used as an extracting agent for sulfur compounds. The process involves dissolving the ionic liquid in acetone, adjusting the pH with sodium hydroxide to form a precipitate, filtering the solution to remove the precipitate from the solution, removing the solvent from the filtrate by evaporation under reduced pressure, dissolving the residue obtained in acetone, filtering the solution to remove the precipitate, adjusting the pH of the solution by adding hydrochloric acid to a pH range of 2-7 and heating the regenerated ionic liquid to 70-80° C., under reduced pressure until dry. The process disclosed in U.S. Pat. No. 8,597,517 employes strong base such as sodium hydroxide which precipitates aluminium as $Al(OH)_3$ and generates HCl. Thus, recovering and recycling of aluminium trichloride is difficult.

The drawbacks associated with the processes of the prior art are that the purity of the catalyst recovered/regenerated is poor and cannot be reused/recycled beyond certain limit. Further, some of the processes require specialized apparatus leading to heavy investments in equipment. Still further, in some of the prior art processes, the conditions employed are severe and therefore, energy inefficient.

Therefore, there is felt a need for a simple and economic process for regenerating ionic compound having high purity and recycleability and which utilizes alternative solvents and bases which can be employed to effectively regenerate the ionic compound.

Objects:

Some of the objects of the present disclosure, which at least one embodiment herein satisfies, are as follows:

It is an object of the present disclosure to provide a process for regenerating ionic compound.

It is another object of the present disclosure to provide a process for regenerating ionic compound which is efficient, simple and economic.

It is still another object of the present disclosure to provide a high yielding process for regenerating ionic compound.

It is still another object of the present disclosure to provide a process for regenerating ionic compound having high purity.

Other objects and advantages of the present disclosure will be more apparent from the following description, which are not intended to limit the scope of the present disclosure.

SUMMARY

The present disclosure provides a process for regenerating an ionic compound selected from the group consisting of ionic compound of Formula A and ionic compound of Formula B from an adduct of ionic compound of Formula A or B, conjunct polymers and at least one metal chloride,

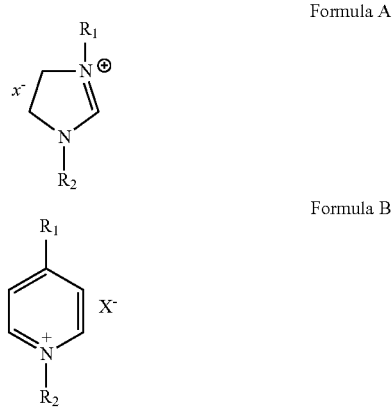

wherein $R_1$ and $R_2$ are independently alkyl group and X is a halogen.

said process comprising the following steps:
a) adding ethyl acetate to said adduct to dissolve the conjunct polymers in ethyl acetate and incorporating at least a base to form a solid complex of the ionic compound of Formula A or B, the metal chloride and the base;
b) filtering said complex to separate a complex residue and ethyl acetate containing conjunct polymers; and
c) washing at least once said complex residue with dichlorormethane to obtain the ionic compound of formula A or B and an adduct of metal chloride and the base.

Typically, $R_1$ and $R_2$ are independently selected from the group consisting of methyl, ethyl, propyl and butyl.

Typically, the halogen is selected from the group consisting of bromine and chlorine.

Typically, the metal chloride is aluminium trichloride.

Typically, base is selected from the group consisting of triethylamine, tert-butyl amine, sodium carbonate, sodium bicarbonate, potassium carbonate, potassium bicarbonate, ammonium carbonate and combinations.

Typically, the step (a) is carried out at a temperature ranging from 20° C. to 50° C.

Typically, the process further includes steps of recovering and recycling of ethyl acetate and dichloromethane.

Typically, the step (a) includes adjusting the pH value in the range of 7 to 7.5.

Typically, said process characterized in that the recovery of the ionic compound ranges from 60 to 99%.

BRIEF DESCRIPTION OF THE ACCOMPANYING DRAWING

FIG. 1 illustrates the process of the present disclosure for regenerating ionic compound.

DETAILED DESCRIPTION

The present disclosure provides regeneration of deactivated or exhausted ionic compound in a simple and an effective manner.

The deactivated or exhausted ionic compound is typically contaminated with conjunct polymers. The process of regeneration of ionic compound mainly involves mixing a deactivated ionic compound with at least one solvent such as ethyl acetate and neutralizing with at least one base to obtain a precipitate. The obtained precipitate is filtered to obtain a residue which is then washed with a solvent such as dichloromethane to obtain the ionic compound.

The present disclosure focused on utilization of two solvent systems. In accordance with the present disclosure the first solvent employed includes but is not limited to ethyl acetate which dilutes the deactivated ionic compound and dissolves the conjunct polymer. However, the ionic compound is found to be not soluble in the first solvent. The present disclosure further utilizes specific organic bases such as triethylamine, tert-butyl amine, sodium carbonate, sodium bicarbonate, potassium carbonate, potassium bicarbonate, ammonium carbonate and combinations to neutralize the ionic compound and form a complex of ionic compound and metal chloride with the base.

The conjunct polymers dissolved in ethyl acetate are removed by filtration. The ionic compound is isolated from the complex by washing with another solvent, namely dichloromethane. The base-metal chloride adduct is formed as a by-product which can be utilized for other applications. Alternatively, metal chloride can be further separated from the adduct.

It is found that the combination of two different solvents is essential to obtain the ionic compound from the deactivated ionic compound. Further, it is also found that the use of strong bases such as NaOH and KOH precipitates metal e.g. aluminium is precipitated as $Al(OH)_3$ with liberation of HCl and it is difficult to recover aluminium trichloride. Thus, the process becomes inefficient and uneconomic.

In one embodiment the present disclosure provides a process for regenerating an compound selected from the group consisting of ionic compound of Formula A and ionic compound of Formula B from an adduct of ionic compound of Formula A or B, conjunct polymers and at least one metal chloride,

Formula B

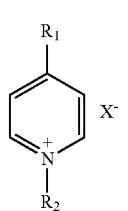

wherein $R_1$ and $R_2$ are independently alkyl group and X is a halogen.

In one embodiment, $R_1$ and $R_2$ are independently selected from the group consisting of methyl, ethyl, propyl and butyl and halogen is selected from the group consisting of bromine and chlorine.

The process involves the following steps:

In the first step, ethyl acetate is added to the adduct in order to dissolve the conjunct polymers from the adduct in ethyl acetate and at least one base is incorporated to form a solid complex of the ionic compound of formula A or B and the metal chloride and the base. The step of forming a complex is carried out at a temperature ranging from 20° C. to 50° C. and it include adjusting the pH value in the range of 7 to 7.5. The base employed includes but is not limited to triethylamine, tert-butyl amine, sodium carbonate, sodium bicarbonate, potassium carbonate, potassium bicarbonate, ammonium carbonate and combinations. In one embodiment, the metal chloride is aluminium trichloride.

The obtained complex is filtered to separate a complex residue and ethyl acetate containing conjunct polymers.

In the next step, the complex residue is washed at least once with dichlorormethane to obtain the ionic compound of formula A or B and an adduct of metal chloride and the base.

The process of the present disclosure further includes steps of recovering and recycling of ethyl acetate and dichloromethane.

The present disclosure the process is illustrated with the help of non-limiting accompanying drawing (FIG. 1) wherein, (102) represents a pre-mixer, the pre-mixer can be either a stirred vessel or static mixer or jet mixer or pump mixer;

(104) represents a neutralization reactor, the neutralization reactor can be a stirred tank reactor or a static mixer or a combination thereof;

(106) represents a first filter, the filter (106) can be a centrifuge or pressure nutsche filter or agitated nutsche filter dryer or agitated thin film dryer;

(108) represents an extractor, the extractor can be a simple stirred vessel or a counter current extractor;

(110) represents a second filter, the filter (110) can be a centrifuge or pressure nutsche filter or agitated nutsche filter dryer or agitated thin film dryer;

(112) represents a distillation column, the distillation column (112) can be a tray column or packed column or falling film evaporator;

(114) represents an evaporator, the evaporator (114) can be single effect or multi-effect evaporator or falling film evaporator or agitated thin film evaporator or falling film evaporator followed by agitated thin film evaporator;

(116) represents a neutralization reactor;

(118) represents a third filter, the filter (118) can be a centrifuge or pressure nutsche filter or agitated nutsche filter dryer or agitated thin film dryer; and (120) represents a distillation column, the distillation can be a tray column or packed column or falling film evaporator.

The process of the present disclosure is described hereinafter. Deactivated ionic compound is premixed with a first suitable solvent in a pre-mixer (102) to obtain a mixture. The suitable solvent used for mixing with deactivated ionic compound includes but is not limited to ethyl acetate The mixture is then transferred to a neutralization reactor (104) and a first suitable base is fed to the neutralization reactor (104) where the neutralization of ionic compound occurs. The neutralization of the mixture containing ionic compound is carried out at a temperature ranging between 20° C. and 50° C. The first base utilized for neutralizing the mixture includes but is not limited to triethylamine, tert-butyl amine, carbonate, sodium bicarbonate, potassium carbonate, potassium bicarbonate and ammonium carbonate. During neutralization process the base-metal complex is precipitated. The reaction mass comprising the base-metal complex is filtered through a filter (106) wherein the reaction mass is separated into the residue and filtrate. The residue may be iteratively washed with a washing solvent to ensure the complete removal of conjunct polymer.

The filtrate obtained after the filtration contains solvent and dissolved conjunct polymer which is subject to distillation in a distillation column (112) for recovery of solvent. The recovered solvent is then recycled for further use.

The residue obtained after filtration is then extracted using a second suitable solvent in an extractor (108) and then filtered through a filter (110) to remove ionic compound to obtain a residue containing base-metal complex and a filtrate containing the second solvent and ionic compound. The residue is repeatedly washed with a washing solvent solvent to ensure that no traces of ionic compound are left in the residue. Though the washing solvent used for washing the residue can be different from the second solvent used for extraction, the use of same solvent for both extraction and washing would be appreciated for economic and process feasibility reasons. The filtrate containing solvent and ionic compound salt is fed to an evaporator (114) where the solvent is recovered. The recovered solvent then may be recycled into the process of the present disclosure, optionally, after further purification. The compound obtained after recovery of the solvent is a regenerated ionic compound.

The residue containing base-metal complex is contacted with dilute methanolic solution of a second base in the neutralization reactor (116) wherein the complex reacts with the second base to give slurry containing metal hydroxide solids, base and methanol. The second base used for reacting with the base-metal complex is a strong base which includes but is not limited to sodium hydroxide and potassium hydroxide. The reaction of the complex with the second base is carried out a temperature in the range of 20° C. to 50° C. The slurry mass is then filtered through a filter (118) to separate the metal hydroxide solids and the first base. The filtrate obtained after filtration contains mixture of the first base and methanol which is then separated in column (120). The first base separated in column (120) may be then recycled for neutralization of the mixture containing deactivated ionic compound. The methanol separated may also be recycled and reused.

The details of the disclosure will further be explained by the way of examples which do not limit the scope of the disclosure.

Example 1

In this experiment, chloroaluminate based ionic compound was prepared which was deactivated by using it repeatedly for alkylation reaction and then the deactivated ionic compound was regenerated by a process of the present disclosure.

Step i: Preparation of Chloroaluminate Ionic Compound with 1-Butyl-3-Methyl Imidazolium Bromide [BMIM]Br The setup consisted of a 5 L three neck RB flask fitted with an overhead stirrer and placed in an ice bath at 0-5° C. The flask was clamped to provide stability under stirring. The whole assembly was kept under nitrogen atmosphere. 680 gm of [BMIM]Br was weighed and carefully charged into the flask through a funnel 830 gm of $AlCl_3$ was weighed and added slowly into the flask with constant stirring. The charging of $AlCl_3$ was completed in 1.5 hrs. The mixture was further stirred for 2 hrs to mix the raw materials properly. The final catalyst was kept under nitrogen conditions.

Step ii: Deactivation of Ionic Compound Prepared in Step (i) by Using it Repeatedly for Alkylation Reaction 92 lit of olefin stream containing 10-15% C10 to C14 olefins and 36 lit of benzene were added into a 250 lit round bottom reactor kept inside a heating mantle. The agitator was started and heating coils were switched on. When the mixture attains the temperature of 45° C., 1.3 kg of the catalyst prepared in step (i) was charged and stirred for 10 mins. After 10 mins the hydrocarbon and catalyst layers were separated and the bottom catalyst layer was recycled back with the same quantities of fresh olefin stream and benzene.

Step iii: Regeneration of Ionic Compound Using the Process of the Present Disclosure Employing Triethylamine 209 gm of deactivated catalyst of chloroaluminate ionic compound with 1-butyl-3-methyl imidazolium bromide (obtained in step ii) and 269.1 gm of ethyl acetate were charged into a 2 lit neutralization reactor (104) equipped with an overhead stirrer, the reactor is placed in a water bath maintained at 25-30° C. The mixture was stirred for 5 mins. Triethylamine is added slowly into the neutralization reactor until the pH of the reaction mass changes from acidic (pH: 1-2) to neutral (pH: 7-7.5). Approximately 192.13 gm of triethylamine was added over a time period of 1 hr. Once neutral pH was achieved, triethylamine addition was stopped and the reaction was further stirred for 45 mins. The reaction mass was kept without stirring for 1.5 hrs to allow the solids to settle at the bottom. The reaction mass was then transferred from the reactor to a nutsche filter (106) and filtered under vacuum. Residue was washed with 640.45 gm of ethyl acetate. The filtrate obtained from the nutsche filter (106) was charged into a distillation column (112) where ethyl acetate is separated as distillate at atmospheric conditions. The bottom residue contains 26 gm of conjunct polymer and hydrocarbon mixture.

The residue obtained from the nutsche filter (106) was charged into an extractor (108) equipped with an overhead stirrer. To it, 532 gm of dichloromethane was added and stirred for 30 mins. The temperature was kept at 25-30° C. The slurry obtained from the extractor was charged into a nutsche filter (110) and filtered under vacuum. During filtration the residue was washed with 308 gm of dichloromethane. The filtrate (dichloromethane layer) obtained from the nutsche filter (110) was charged into an evaporation column (114) fitted with a horizontal condenser. The dichloromethane is recovered by distillation. 82.5 gm of residue containing was obtained which was analyzed for Br and Al content. The yield obtained was 78%.

274 gm of cake obtained from the filter (110) was charged into a neutralization reactor (116) followed by addition of 375 gm of 20% methanolic KOH solution and stirring for a time period of 30 mins to obtain slurry. The slurry was then filtered through a nutsche filter (118) under vacuum. The filtrate obtained was subjected to distillation column (120) to recover methanol as distillate and 180 gm of triethylamine (90% purity) as a bottom product, which can be further distilled in a separate column to get pure TEA.

Example 2

[BMIM]Br Recovery from the Fresh Catalyst by Neutralizing with Triethylamine

In this experiment, ionic compound prepared in step (i) of experiment 1 was regenerated directly without being deactivating to study the efficiency of the process of the present disclosure.

10.0 gm of fresh catalyst obtained from step (i) of experiment 1 was charged along with 50 ml ethyl acetate into a 250 ml RB flask kept with an overhead stirrer, maintained at 29° C. Slowly 12.6 gm of triethylamine is added over a period of 1 hr and stirred for 30 mins. The mixture thus obtained is filtered and ethyl acetate layer is separated. The solids obtained were washed with 200 ml dichloromethane in lot wise to extract [BMIM]Br from the solid mixture. The dichloromethane layer thus obtained is distilled off to get 4 gm of [BMIM]Br salt. The yield obtain was 88%.

Example 3

Regeneration of Ionic Compound [BMIM]Br Using the Process of the Present Disclosure Employing Sodium Carbonate The process used in this experiment is same as described in step (iii) of experiment 1 except that sodium carbonate solution is used instead of triethyl amine.

100 gm of deactivated catalyst obtained in step (ii) of experiment 1 was charged into a 500 ml conical flask. $Na_2CO_3$ solution is prepared by mixing 133.3 gm of $Na_2CO_3$ and 350 ml water and kept a side. The $Na_2CO_3$ solution prepared was added slowly to the conical flask containing deactivated catalyst. Once the addition was complete, 100 ml of ethyl acetate was added to the flask and stirred for 1 hr and allowed to settle for 1 hr. The water and ethyl acetate layers were separated and water layer was subjected to distillation to give solid mixture. The solid mixture was washed with 75 ml of dichloromethane to extract [BMIM]Br and the dichloromethane layer obtained was distilled off to get 25 gm of [BMIM]Br salt. The ethyl acetate layer was distilled off to give 11 gm of conjunct polymer and organics. The [BMIM]Br salt obtained was analyzed for Br and Al content. The yield obtained was 62.5%.

Example 4

Regeneration of Ionic Compound [BMIM]Br Using the Process of the Present Disclosure Employing Tert-Butylamine The process used in this experiment is same as described in step (iii) of experiment 1 except that tert-butylamine is used instead of triethyl amine.

10.19 gm of deactivated catalyst obtained in step (ii) of experiment 1 was charged along with 50 ml ethyl acetate into a 250 ml RB flask kept with an overhead stirrer, maintained at 29° C. Slowly 25 ml of tert-butylamine was added over a period of 1 hr and stirred for 30 mins. The mixture thus obtained was filtered, the ethyl acetate layer obtained after filtration contains conjunct polymer and organics. The solids obtained were washed with 100 ml dichloromethane to extract [BMIM]Br from the solid mixture. The dichloromethane layer thus obtained was distilled off to get 1.1 gm of [BMIM]Br salt.

Example 5

Regeneration of Ionic Compound [BMIM]Br Using the Process of the Present Disclosure Employing Ammonia Solution The process used in this experiment is same as described in step (iii) of experiment 1 except that ammonia solution is used instead of triethyl amine.

10.09 gm of deactivated catalyst obtained in step (ii) of experiment 1 was charged along with 50 ml ethyl acetate into a 250 ml RB flask kept with an overhead stirrer, maintained at 29° C. Slowly 4.25 gm of 25% $NH_3$ solution was added over a period of 1 hr and stirred for 30 mins. The mixture thus obtained was filtered. The ethyl acetate layer obtained after filtration contains conjunct polymer and organics. The solids obtained were washed with 200 ml dichloromethane in lot wise to extract [BMIM]Br from the solid mixture. The dichloromethane layer thus obtained was distilled off to get 1.1 gm of [BMIM]Br salt.

Example 6

In this experiment, chloroaluminate based ionic compound was prepared which was deactivated by using it repeatedly for alkylation reaction and then the deactivated ionic compound was regenerated by a process of the present disclosure.

Step i: Preparation of Chloroaluminate Ionic Compound with 1-Butyl-3-Methyl Imidazolium Chloride [BMIM]Cl A setup consisting of a 5 L three neck RB flask fitted with an overhead stirrer was placed in an ice bath at 0-5° C. The flask was clamped to provide stability under stirring. The whole assembly was kept under nitrogen atmosphere. 542 gm of [BMIM]Cl was weighed and carefully charged into the flask through a funnel. 830 gm of $AlCl_3$ was weighed and added slowly into the flask with constant stirring. The charging of $AlCl_3$ was completed in 1.5 hrs. The mixture was further stirred for 2 hrs to mix the raw materials properly. The final catalyst (ionic compound) was kept under nitrogen conditions.

Step ii: Deactivation of Ionic Compound Prepared in Step (i) by Using it Repeatedly for Alkylation Reaction 92 lit of olefin stream containing 10-15% of $C_{10}$ to $C_{14}$ olefins and 36 lit of benzene were added into a 250 lit round bottom reactor kept inside a heating mantle. The agitator was started and heating coils were switched on. When the mixture attains the temperature of 45° C., 1.3 kg of the catalyst prepared in step (i) was charged and stirred for 10 mins. After 10 mins the hydrocarbon and catalyst layers were separated and the bottom catalyst layer was recycled back with the same quantities of fresh olefin stream and benzene.

Step iii: Regeneration of Ionic Compound Using the Process of the Present Disclosure Employing Triethylamine 209 gm of deactivated catalyst of chloroaluminate ionic compound with 1-butyl-3-methyl imidazolium chloride (obtained in step ii) and 269.1 gm of ethyl acetate were charged into a 2 liter neutralization reactor (104) equipped with an overhead stirrer, the reactor is placed in a water bath maintained at 25-30° C. The mixture was stirred for 5 mins. Triethylamine is added slowly into the neutralization reactor until the pH of the reaction mass changes from acidic (pH: 1-2) to neutral (pH: 7-7.5). Approximately 192.13 gm of triethylamine was added over a time period of 1 hr. Once neutral pH was achieved, triethylamine addition was stopped and the reaction was further stirred for 45 mins. The reaction mass was kept without stirring for 1.5 hrs to allow the solids to settle at the bottom. The reaction mass was then transferred from the reactor to a nutsche filter (106) and filtered under vacuum. Residue was washed with 640.45 gm of ethyl acetate. The filtrate obtained from the nutsche filter (106) was charged into a distillation column (112) where ethyl acetate is separated as distillate at atmospheric conditions. The bottom residue contains 26 gm of conjunct polymer and hydrocarbon mixture.

The residue obtained from the nutsche filter (106) was charged into an extractor (108) equipped with an overhead stirrer. To it, 532 gm of dichloromethane was added and stirred for 30 mins. The temperature was kept at 25-30° C. The slurry obtained from the extractor was charged into a nutsche filter (110) and filtered under vacuum. During filtration the residue was washed with 308 gm of dichloromethane. The filtrate (dichloromethane layer) obtained from the nutsche filter (110) was charged into an evaporation column (114) fitted with a horizontal condenser. The dichloromethane is recovered by distillation. 82.5 gm of residue containing was obtained which was analyzed for Cl and Al content. The yield obtained was 80%.

274 gm of residue obtained from the filter (110) was charged into a neutralization reactor (116) followed by addition of 375 gm of 20% methanolic KOH solution and stirring for a time period of 30 mins to obtain slurry. The slurry was then filtered through a nutsche filter (118) under vacuum. The filtrate obtained was subjected to distillation column (120) to recover methanol as distillate and 180 gm of triethylamine (90% purity) as a bottom product.

Example 7

[BMIM]Cl Recovery from the Fresh Catalyst by Neutralizing with Triethylamine

In this experiment, ionic compound prepared in step (i) of example 6 was regenerated directly without being deactivating to study the efficiency of the process of the present disclosure.

10.0 gm of fresh catalyst obtained from step (i) of example 6 was charged along with 50 ml ethyl acetate into a 250 ml RB flask kept with an overhead stirrer, maintained at 29° C. Slowly 12.6 gm of triethylamine is added over a period of 1 hr and stirred for 30 mins. The mixture thus obtained is filtered. The ethyl acetate layer thus obtained contains conjunct polymer and organics. The solids obtained were washed with 200 ml dichloromethane in lot wise to extract [BMIM]Cl from the solid mixture. The dichloromethane layer thus obtained is distilled off to get 3.8 gm of [BMIM]Cl salt. The yield obtain was 87%.

Example 8

Regeneration of Ionic Compound [BMIM]Cl Using the Process of the Present Disclosure Employing Sodium Carbonate The process used in this experiment is same as described in step (iii) of example 6 except that sodium carbonate solution is used instead of triethyl amine.

100 gm of deactivated catalyst obtained in step (ii) of example 6 was charged into a 500 ml conical flask. $Na_2CO_3$ solution is prepared by mixing 133.3 gm of $Na_2CO_3$ and 350 ml water and kept a side. The $Na_2CO_3$ solution prepared was added slowly to the conical flask containing deactivated catalyst. Once the addition was complete, 100 ml of ethyl acetate was added to the flask and stirred for 1 hr and allowed to settle for 1 hr. The water and ethyl acetate layers were separated and water layer was subjected to distillation to give solid mixture. The solid mixture was washed with 75 ml of dichloromethane to extract [BMIM]Cl and the dichloromethane layer obtained was distilled off to get 24 gm of [BMIM]Cl salt. The ethyl acetate layer was distilled off to give 11 gm of conjunct polymer and organics. The [BMIM]Cl salt obtained was analyzed for Cl and Al content. The yield obtained was 63%.

Example 9

Regeneration of Ionic Compound [BMIM]Cl Using the Process of the Present Disclosure Employing Tert-Butylamine The process used in this experiment is same as described in step (iii) of example 6 except that tert-butylamine is used instead of triethyl amine.

10.19 gm of deactivated catalyst obtained in step (ii) of example 6 was charged along with 50 ml ethyl acetate into a 250 ml RB flask kept with an overhead stirrer, maintained at 29° C. Slowly 25 ml of tert-butylamine was added over a period of 1 hr and stirred for 30 mins. The mixture thus obtained was filtered, the ethyl acetate layer obtained after filtration contains conjunct polymer and organics. The solids obtained were washed with 100 ml dichloromethane to extract [BMIM]Cl from the solid mixture. The dichloromethane layer thus obtained was distilled off to get 1.2 gm of [BMIM]Cl salt.

Example 10

Regeneration of Ionic Compound [BMIM]Cl Using the Process of the Present Disclosure Employing Ammonia Solution The process used in this experiment is same as described in step (iii) of example 6 except that ammonia solution is used instead of triethyl amine.

10.09 gm of deactivated catalyst obtained in step (ii) of example 6 was charged along with 50 ml ethyl acetate into a 250 ml RB flask kept with an overhead stirrer, maintained at 29° C. Slowly 4.25 gm of 25% $NH_3$ solution was added over a period of 1 hr and stirred for 30 mins. The mixture thus obtained was filtered. The ethyl acetate layer obtained after filtration contains conjunct polymer and organics. The solids obtained were washed with 200 ml dichloromethane in lot wise to extract [BMIM]Cl from the solid mixture. The dichloromethane layer thus obtained was distilled off to get 1.2 gm of [BMIM]Cl salt.

Example 11

In this experiment, chloroaluminate based ionic compound was prepared which was deactivated by using it repeatedly for alkylation reaction and then the deactivated ionic compound was regenerated by a process of the present disclosure.

Step i: Preparation of Chloroaluminate Ionic Compound with 1-Butyl-4-Methylpyridinium Chloride [BMPy]Cl The setup consisting of a 5 L three neck RB flask fitted with an overhead stirrer was placed in an ice bath at 0-5° C. The flask was clamped to provide stability under stirring. The whole assembly was kept under nitrogen atmosphere. 576.2 gm of [BMPyC]Cl was weighed and carefully charged into the flask through a funnel 830 gm of $AlCl_3$ was weighed and added slowly into the flask with constant stirring. The charging of $AlCl_3$ was completed in 1.5 hrs. The mixture was further stirred for 2 hrs to mix the raw materials properly. The final catalyst (ionic compound) was kept under nitrogen conditions.

Step ii: Deactivation of Ionic Compound Prepared in Step (i) by Using it Repeatedly for Alkylation Reaction 92 lit of olefin stream containing 10-15% $C_{10}$ to $C_{14}$ olefins and 36 lit of benzene were added into a 250 lit round bottom reactor kept inside a heating mantle. The agitator was started and heating coils were switched on. When the mixture attains the temperature of 45° C., 1.3 kg of the catalyst prepared in step (i) was charged and stirred for 10 mins. After 10 mins the hydrocarbon and catalyst layers were separated and the bottom catalyst layer was recycled back with the same quantities of fresh olefin stream and benzene.

Step iii: Regeneration of Ionic Compound Using the Process of the Present Disclosure Employing Triethylamine 209 gm of deactivated catalyst of chloroaluminate ionic compound with 1-butyl-4-methylpyridinium chloride (obtained in step ii) and 269.1 gm of ethyl acetate were charged into a 2 lit neutralization reactor (104) equipped with an overhead stirrer, the reactor is placed in a water bath maintained at 25-30° C. The mixture was stirred for 5 mins. Triethylamine is added slowly into the neutralization reactor until the pH of the reaction mass changes from acidic (pH: 1-2) to neutral (pH: 7-7.5). Approximately 192.13 gm of triethylamine was added over a time period of 1 hr. Once neutral pH was achieved, triethylamine addition was stopped and the reaction was further stirred for 45 mins. The reaction mass was kept without stirring for 1.5 hrs to allow the solids to settle at the bottom. The reaction mass was then transferred from the reactor to a nutsche filter (106) and filtered under vacuum. Residue was washed with 640.45 gm of ethyl acetate. The filtrate obtained from the nutsche filter (106) was charged into a distillation column (112) where ethyl acetate is separated as distillate at atmospheric conditions. The bottom residue contains 26 gm of conjunct polymer and hydrocarbon mixture.

The residue obtained from the nutsche filter (106) was charged into an extractor (108) equipped with an overhead stirrer. To it, 532 gm of dichloromethane was added and stirred for 30 mins. The temperature was kept at 25-30° C. The slurry obtained from the extractor was charged into a nutsche filter (110) and filtered under vacuum. During filtration the residue was washed with 308 gm of dichloromethane. The filtrate (dichloromethane layer) obtained from the nutsche filter (110) was charged into an evaporation column (114) fitted with a horizontal condenser. The dichloromethane is recovered by distillation. 84.5 gm of residue containing was obtained which was analyzed for Cl and Al content. The yield obtained was 83%.

278 gm of residue obtained from the filter (110) was charged into a neutralization reactor (116) followed by addition of 375 gm of 20% methanolic KOH solution and stirring for a time period of 30 mins to obtain slurry. The slurry was then filtered through a nutsche filter (118) under vacuum. The filtrate obtained was subjected to distillation column (120) to recover methanol as distillate and 180 gm of triethylamine (90% purity) as a bottom product.

Example 12

[BMPy]Cl Recovery from the Fresh Catalyst by Neutralizing with Triethylamine

In this experiment, ionic compound prepared in step (i) of example 11 was regenerated directly without being deactivating to study the efficiency of the process of the present disclosure.

11.0 gm of fresh catalyst obtained from step (i) of example 6 was charged along with 50 ml ethyl acetate into a 250 ml RB flask kept with an overhead stirrer, maintained at 29° C. Slowly 12.9 gm of triethylamine is added over a period of 1 hr and stirred for 30 mins. The mixture thus obtained is filtered. The ethyl acetate layer thus obtained contains conjunct polymer and organics. The solids obtained were washed with 200 ml dichloromethane in lot wise to extract [BMPy]Cl from the solid mixture. The dichloromethane layer thus obtained is distilled off to get 3.7 gm of [BMP]Cl salt. The yield obtain was 85%.

Example 13

Regeneration of Ionic Compound [BMPy]Cl Using the Process of the Present Disclosure Employing Sodium Carbonate

The process used in this example is same as described in step (iii) of example 6 except that sodium carbonate solution is used instead of triethyl amine.

100 gm of deactivated catalyst obtained in step (ii) of example 6 was charged into a 500 ml conical flask. $Na_2CO_3$ solution is prepared by mixing 133.3 gm of $Na_2CO_3$ and 350 ml water and kept a side. The $Na_2CO_3$ solution prepared was added slowly to the conical flask containing deactivated catalyst. Once the addition was complete, 100 ml of ethyl acetate was added to the flask and stirred for 1 hr and allowed to settle for 1 hr. The water and ethyl acetate layers were separated and water layer was subjected to distillation to give solid mixture. The solid mixture was washed with 75 ml of dichloromethane to extract [BMPy]Cl and the dichloromethane layer obtained was distilled off to get 23 gm of [BMPy]Cl salt. The ethyl acetate layer was distilled off to give 11.5 gm of conjunct polymer and organics. The [BMPy]Cl salt obtained was analyzed for Cl and Al content. The yield obtained was 62%.

Example 14

Regeneration of Ionic Compound [BMPy]Cl Using the Process of the Present Disclosure Employing Tert-Butylamine

The process used in this example is same as described in step (iii) of example 11 except that tert-butylamine is used instead of triethyl amine.

10.5 gm of deactivated catalyst obtained in step (ii) of example 11 was charged along with 50 ml ethyl acetate into a 250 ml RB flask kept with an overhead stirrer, maintained at 29° C. Slowly 25 ml of tert-butylamine was added over a period of 1 hr and stirred for 30 mins. The mixture thus obtained was filtered, the ethyl acetate layer obtained after filtration contains conjunct polymer and organics. The solids obtained were washed with 100 ml dichloromethane to extract [BMPy]Cl from the solid mixture. The dichloromethane layer thus obtained was distilled off to get 1.3 gm of [BMPy]Cl salt.

Example 15

Regeneration of Ionic Compound [BMPy]Cl Using the Process of the Present Disclosure Employing Ammonia Solution

The process used in this example is same as described in step (iii) of example 11 except that ammonia solution is used instead of triethyl amine.

10.5 gm of deactivated catalyst obtained in step (ii) of example 11 was charged along with 50 ml ethyl acetate into a 250 ml RB flask kept with an overhead stirrer, maintained at 29° C. Slowly 4.4 gm of 25% $NH_3$ solution was added over a period of 1 hr and stirred for 30 mins. The mixture thus obtained was filtered. The ethyl acetate layer obtained after filtration contains conjunct polymer and organics. The solids obtained were washed with 200 ml dichloromethane in lot wise to extract [BMPy]Cl from the solid mixture. The dichloromethane layer thus obtained was distilled off to get 1.3 gm of [BMPy]Cl salt.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A process for regenerating an ionic compound selected from the group consisting of ionic compound of Formula A and ionic compound of Formula B from an adduct of ionic compound of Formula A or B, conjunct polymers and at least one metal chloride,

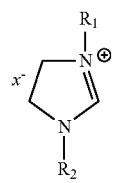

Formula A

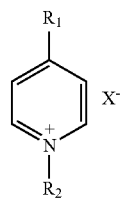

Formula B wherein $R_1$ and $R_2$ are independently alkyl group and X is a halogen;

said process comprising the following steps:

a) adding ethyl acetate to said adduct to dissolve the conjunct polymers in ethyl acetate and incorporating at least a base to form a solid complex of the ionic compound of Formula A or B, the metal chloride and the base;

b) filtering said complex to separate a complex residue and ethyl acetate containing conjunct polymers; and c) washing at least once said complex residue with dichlorormethane to obtain the ionic compound of formula A or B and an adduct of metal chloride and the base.

2. The process as claimed in claim 1, wherein $R_1$ and $R_2$ are independently selected from the group consisting of methyl, ethyl, propyl and butyl.

3. The process as claimed in claim 1, wherein the halogen is selected from the group consisting of bromine and chlorine.

4. The process as claimed in claim 1, wherein the metal chloride is aluminium trichloride.

5. The process as claimed in claim 1, wherein base is selected from the group consisting of triethylamine, tert-butyl amine, sodium carbonate, sodium bicarbonate, potassium carbonate, potassium bicarbonate, ammonium carbonate and combinations.

6. The process as claimed in claim 1, wherein the step (a) is carried out at a temperature ranging from 20° C. to 50° C.

7. The process as claimed in claim 1, include steps of recovering and recycling of ethyl acetate and dichloromethane.

8. The process as claimed in claim 1, wherein the step (a) includes adjusting the pH value in the range of 7 to 7.5.

9. The process as claimed in claim 1, wherein the recovery of the ionic compound ranges from 60 to 99%.

* * * * *